United States Patent [19]
Schaetzle

[11] Patent Number: 5,443,069
[45] Date of Patent: Aug. 22, 1995

[54] THERAPEUTIC ULTRASOUND APPLICATOR FOR THE UROGENITAL REGION

[75] Inventor: Ulrich Schaetzle, Roettenbach, Germany

[73] Assignee: Siemens Aktieng sellschaft, Munich, Germany

[21] Appl. No.: 136,258

[22] Filed: Oct. 15, 1993

[30] Foreign Application Priority Data

Nov. 16, 1992 [DE] Germany .......... 42 38 645.4

[51] Int. Cl.⁶ .......... A61B 8/12
[52] U.S. Cl. .......... 128/660.03; 601/2; 601/3; 607/97
[58] Field of Search ........ 128/24 AA, 24 EL, 660.03; 607/97; 601/2-4

[56] References Cited

U.S. PATENT DOCUMENTS

| | | | |
|---|---|---|---|
| 4,947,830 | 8/1990 | Rattner et al. | 128/24 EL |
| 4,957,099 | 9/1990 | Hassler | 128/660.03 |
| 4,958,639 | 9/1990 | Uchiyama et al. | 128/660.03 |
| 5,095,908 | 3/1992 | Belikan et al. | 128/24 EL |
| 5,123,404 | 6/1992 | Takayama | 128/24 EL |
| 5,193,527 | 3/1993 | Schafer | 601/4 |

FOREIGN PATENT DOCUMENTS 9317646  9/1993  WIPO .

*Primary Examiner*—Ruth S. Smith
*Attorney, Agent, or Firm*—Hill, Steadman & Simpson

[57] ABSTRACT

An ultrasound applicator for the urogenital region, particularly for treating benign prostate hyperplasia, emits ultrasound waves focused onto a working region lying on the working axis of the ultrasound applicator, the ultrasound waves, as seen in a plane proceeding at a right angle relative to the working axis, having a cross section which can be circumscribed by an envelope that has a first principal axis intersecting the working axis and at least one second principal axis that preferably intersects the first principal axis at a right angle. The length of the first principal axis exceeds the length of the second principal axis or axes.

14 Claims, 2 Drawing Sheets

5,443,069

THERAPEUTIC ULTRASOUND APPLICATOR FOR THE UROGENITAL REGION

BACKGROUND OF THE INVENTION

1. Field of the Invention

The present invention is directed to a therapeutic ultrasound applicator for the urogenital region, particularly for the treatment of benign prostate hyperplasia, the applicator emitting ultrasound waves focused at a working region lying on the working axis of the ultrasound applicator.

2. Description of the Prior Art

Ultrasound applicators of the type generally described above are usually abdominally or rectally applied. In the case of abdominal application, which is more comfortable for the patient, a problem is that direct access to the prostate is blocked by the pubic bone. It is therefore necessary to direct the ultrasound waves into the body obliquely downwardly, proceeding from the central abdomen, with the result that the travel path of the ultrasound waves is relatively long. A greater quantity of acoustic energy must be supplied to the patient as a consequence of the high acoustic losses that occur due to the longer path. Additionally, the locating of the prostate with an ultrasound locating means integrated in the ultrasound applicator becomes more difficult because of the long sound-irradiation paths.

There problems are avoided in the case of rectal application, wherein an ultrasound applicator is introduced into the rectum of the patient to be treated; the problem arises, however that rectal application is partially invasive and is considered extremely unpleasant by the patient. Moreover, the rectum offers only a relatively small opening, so that integrating an ultrasound oscillator having adequate power in a rectally applied ultrasound applicator involves difficulties.

SUMMARY OF THE INVENTION

An object of the present invention is to provide an ultrasound applicator for conducting ultrasound therapy in the urogenital region which can be applied in a way that is comfortable for the patient, preferably non-invasively, and such that no substantial, anatomically dependent limits are present in view of the size of the ultrasound oscillator integrated in the ultrasound applicator.

This object is achieved in a therapeutic ultrasound applicator for the urogenital region, particularly for treating benign prostate hyperplasia, constructed in accordance with the principles of the present invention which emits ultrasound waves for use at a working region lying on the working axis of the ultrasound applicator, the applicator producing ultrasound waves having a cross-section, as seen in a plane proceeding at a right angle relative to the working axis, which can be circumscribed by an envelope that has a first principal axis preferably intersecting the working axis, and at least one second principal axis that preferably intersects the first principal axis at a right angle, the length of the first principal axis exceeding that of the second principal axis (or axes). The ultrasound waves focused by the ultrasound applicator exit from the emission surface thereof, which is shaped such that, when the working region is positioned in the region of the prostate of the patient, the ultrasound waves pass unimpeded between the pelvic bones given introduction of the ultrasound waves into the patient between his scrotum and rectum. It is important that the ultrasound waves not be incident on the pelvic bones because bones highly attenuate ultrasound waves and, when charged with ultrasound, are thus heated to a considerably greater degree than the surrounding tissue, with the result that the patient feels intense pain.

It is thus possible to perineally apply the ultrasound applicator of the invention, such that the first principal axis proceeds essentially parallel to the connecting line between scrotum and rectum. As a result of the fact that the length of the first principal axis exceeds that of the second, an unproblematical passage of the ultrasound waves between the pelvic bones is possible in this case. The length of the first principal axis preferably exceeds that of the second principal axis or axes at least by a factor 1.5, preferably at least by a factor 2. As a consequence of the perineal application, the ultrasound resonators of the ultrasound applicator of the invention are situated just as close to the prostate as in the case of rectal application. An unnecessarily high dose of acoustic energy is thus not applied to the patient. At the same time, beneficial conditions are present for the locating of the prostate with an ultrasound locating system integrated in the ultrasound applicator. Since the application of the ultrasound applicator of the invention ensues non-invasively, there are no significant limitations on the size of the ultrasound resonators contained in the ultrasound applicator, particularly if the application ensues relative to a patient in what is referred to as the lithotomy position, i.e. on his back with spread legs angled at the hip and knee joints, since the perineum is then freely accessible. This type of positioning and application is not unpleasant for the patient. By the way, the term "ultrasound resonator" as used in this specification and the appended claims is to comprise both ultrasound transducers operated at a resonant frequency and ultrasound transducers operated at a frequency different from a resonant frequency.

In a preferred embodiment of the invention the ultrasound applicator contains two substantially circular shaped focused ultrasound resonators that are arrangend in a V-shaped orientation such that their foci lie in the working region. The required cross sectional geometry of the ultrasound waves can thus be realized in a structurally simple way.

The ultrasound applicator has a housing filled with an acoustic propagation medium and an application end closed with a resilient coupling membrane, wherein at least one ultrasound resonator is disposed. A good acoustic coupling between the ultrasound resonator or resonators and the region in the body of the patient to be treated can thus be produced by pressing the ultrasound applicator against the body of the patient with the coupling membrane.

A carrying member for the ultrasound resonator or resonators which has a spherical support surface is provided in the applicator, the support surface cooperating with a corresponding support surface of a support member so that the working zone is adjustable over a spherically curved surface. It is thus possible to displace the working zone in the body of the patient, given an ultrasound applicator pressed against the body surface of the patient, without a relative motion between the coupling membrane and the body surface of the patient being required. An improved adjustability is achieved in an embodiment wherein the support member is axially displaceable relative to the housing.

The ultrasound applicator may contain an ultrasound locating transducer which is part of an ultrasound locating system with which the working zone can be imaged. It is thus possible to easily align the ultrasound applicator relative to the body of the patient such that the region to be treated is located in the working zone of the ultrasound waves. An especially beneficial structure of the ultrasound applicator is achieved if the ultrasound locating transducer is arranged substantially on the working axis, since the ultrasound locating transducer is then located in a space that is essentially free of ultrasound waves when a plurality of ultrasound resonators are employed. Locating the region to be treated is facilitated if the ultrasound locating transducer is displaceable along its longitudinal axis and/or is rotatable therearound.

DESCRIPTION OF THE PREFERRED EMBODIMENTS

Figure 1:
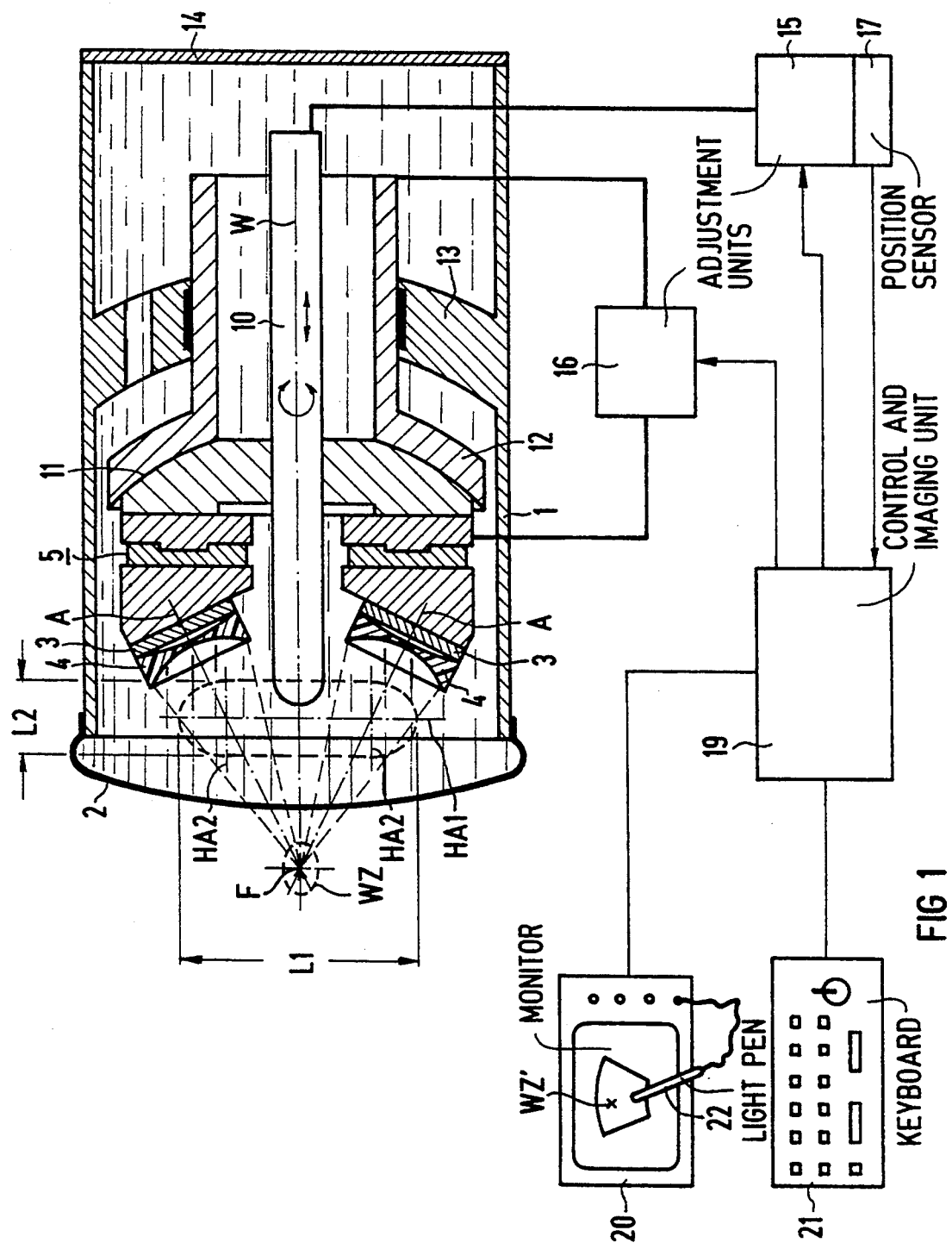
FIG. 1 shows an ultrasound applicator of the invention in a schematic view.
Figure 2:
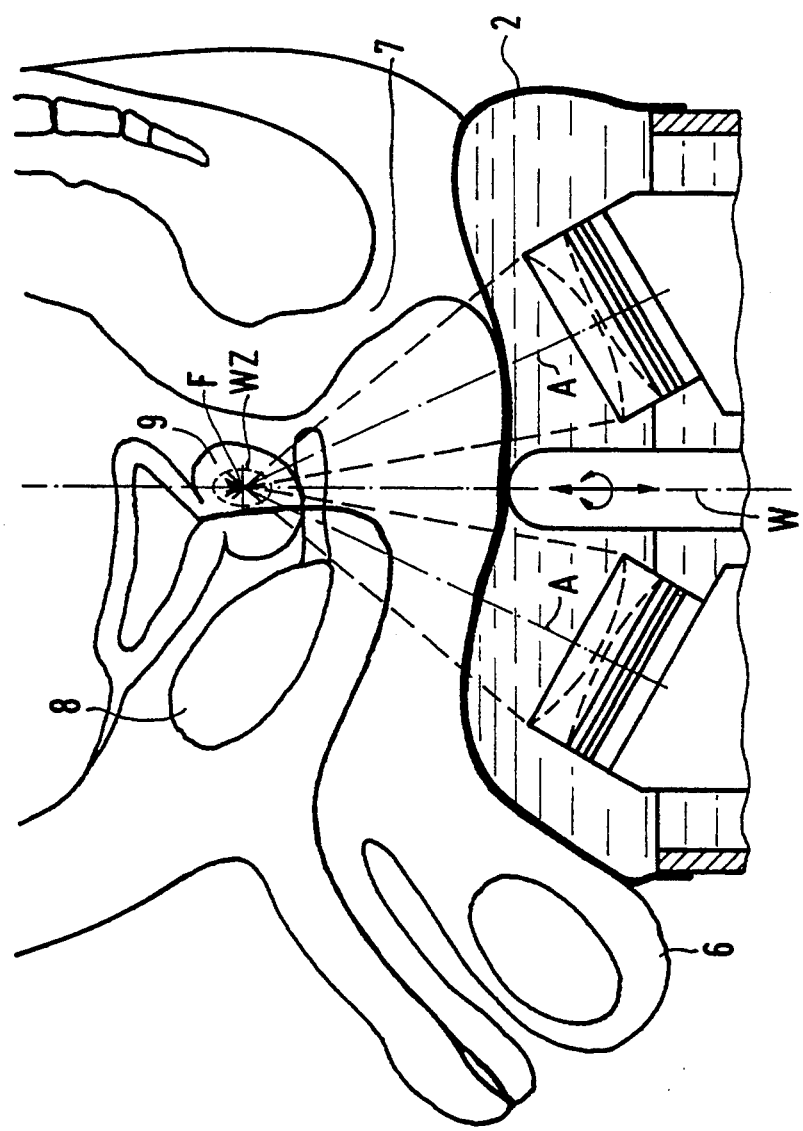
FIG. 2 shows a perineally applied ultrasound applicator of the invention partly in a longitudinal section in order to illustrate the anatomical environment.

As shown in FIG. 1, the ultrasound applicator of the invention has an approximately cylindrical housing 1 filled with a liquid acoustic propagation medium, for example water, and an application end closed with a flexible resilient coupling membrane 2 (also see FIG. 2). This serves the purpose of pressing the ultrasound applicator against the body surface of a patient for acoustic coupling.

Two planar, circular disk-shaped, ultrasound resonators 3, such as piezoelectric transducers, are located inside the housing 1. These being preceded by acoustic positive lenses 4 for focusing the generated ultrasound waves. In the exemplary embodiment described herein, the two ultrasound resonators 3 and the two positive lenses 4 are identical. The positive lenses 4 are glued to the ultrasound resonators 3 in a known way. The ultrasound resonators 3 together with the positive lenses 4 are applied to a carrying member generally referenced 5, which is composed of a plurality of parts. If necessary, acoustic matching layers can be provided in a known way between the ultrasound resonators 3 and the positive lenses 4, and between the ultrasound resonators 3 and the carrying member. Such matching layers are, however, not shown in FIG. 1. The ultrasound resonators can be composed of a plurality of individual resonators stacked on top of one another in a known way (not shown in detail in FIG. 1).

Each of the arrangements composed of ultrasound resonator 3 and an acoustic positive lens 4 has an acoustic axis A along which the ultrasound waves propagate, which converge in a focus F. The ultrasound resonators 3 are applied to the carrying member 5 such that the acoustic axes A intersect with a working axis W of the ultrasound applicator in a point, and such that the foci F lie in this intersection. The foci F then form a working zone WZ which is indicated with broken lines in FIG. 1. In the case of the present exemplary embodiment, the working axis W is the center axis of the ultrasound applicator. As used herein, the working zone WZ means that zone within which the peak pressure of the ultrasound waves is no lower than half the maximum peak pressure in the working zone WZ ($-6$ dB zone). The drive of the ultrasound resonators 3 ensues such with an electric generator contained in a control and imaging unit (described below) so that the ultrasound waves of the two ultrasound resonators 3 are additively superimposed.

As a result of the described arrangement of the ultrasound resonators 3, the ultrasound applicator exhibits an emission surface from which the ultrasound waves emanate. This emission surface has such a shape that the ultrasound waves—as seen in a plane proceeding at a right angle relative to the working axis W—have a cross section that can be circumscribed by an envelope that is composed of two ellipse sections, as entered in broken lines in FIG. 1. Because the respective acoustic axes A intersect, the cross section/envelope is completely occupied by the emitted ultrasound waves. The envelope consequently has a first principal axis HA1 that intersects the working axis W at a right angle and also intersects the acoustic axes A. The first principal axis HA1 has a length of L1. The envelope also has two second principal axes that proceed through the intersections of the first principal axis HA1 with the acoustic axes A and thus intersect both the first principal axis HA1 and each acoustic axis A at a right angle. The two principal axes HA2 each have the length L2 that is shorter than the length L1.

The length L1 of the first principal axis HA1 is longer by at least a factor 1.5, preferably by at least a factor 2.0, than the length L2 of the second principal axes HA2. In the present case, the length L1 is greater than the length L2 by a factor 2.5.

As a result of the described fashioning of the ultrasound applicator, it can be perineally applied in the way shown in FIG. 2, i.e. can be applied between scrotum 6 and rectum 7 without the pelvic bones—which are not shown in FIG. 2 with the exception of the pubic bone 8—constituting an impediment for the access of the ultrasound waves to the prostate 9. The length L1 should exceed the length L2 by no more than the factor 4, since the cross section available for ultrasound irradiation cannot be completely exploited given higher factors.

An ultrasound locating transducer, preferably a B-scan applicator, is accepted in a bore of the carrying member 5, serving the purpose of locating the region to be treated, i.e. the prostate 9. In order to be able to align the ultrasound locating transducer 10 relative to the prostate 9 such that a good image is achieved, the ultrasound locating transducer 10 is accepted in the bore of the carrying member 5 so as to be longitudinally displaceable and rotatable, as indicated in FIG. 1 by appropriate arrows.

As a result of the described arrangement of the ultrasound resonators 3, a space free of ultrasound is present in the region of the working axis W. The ultrasound locating transducer 10, whose longitudinal axis substantially coincides with the working axis W, is arranged in this space free of ultrasound. In the present instance, the arrangement is undertaken such that the ultrasound transducer contained in the ultrasound locating transducer 10 remains in the space free of ultrasound even when the application end of the ultrasound locating transducer 10 presses against the body surface of the patient with the interposition of the coupling membrane 2 in the way shown in FIG. 2. It is thus guaranteed that neither a noteworthy degradation of the ultrasound waves generated with the ultrasound resonators 3 occurs due to the ultrasound locating transducer 10, nor does a degradation of the function of the ultrasound locating transducer 10 occur due to the ultrasound waves.

As may be seen from FIG. 1, the carrying member 5 has a spherically curved support surface 11 at its side facing away from the ultrasound resonators 3. This support surface 11 cooperates with a spherical cap-shaped support surface having a corresponding radius in a support member 12 that is accepted so as to be longitudinally displaceable but non-rotatable in the bore of a housing flange 13. It is thus possible to vary the spatial alignment of the ultrasound resonators 3 and the ultrasound locating transducer 10 relative to the body of the patient without the occurrence of a relative motion between the coupling membrane 2 and the body surface of the patient. This is an important advantage since, due to the many creases in the body surface in the region of the perineum, relative movements between coupling membrane 2 and body surface would inevitably lead to the fact that air bubbles would be present between the two and these would make the locating of the region to be treated as well as the introduction of the ultrasound generated with the ultrasound resonators 3 into the body of the patient more difficult.

That end of the housing 1 distal from the coupling membrane, moreover, is closed by a base 14.

Adjustment units 15 and 16, schematically indicated in FIG. 1, are provided for adjusting the ultrasound locating transducer 10 relative to the carrying member 5 and for adjusting the carrying member 5 together with the ultrasound resonators 3 relative to the housing I and relative to the coupling membrane 2. These adjustment units 15 and 16 are preferably motor-driven adjustment units. A position sensor 17 is schematically indicated in FIG. I allocated to the adjustment unit 15. The position sensor 17 emits output signals corresponding to the current position of the ultrasound locating transducer 10 relative to the carrying member 5. Both adjustment units 15 and 16 as well as the position sensor 17 are connected to a control and imaging unit 19, to which a monitor 20 and a keyboard 21 are connected.

The control and imaging unit 19 cooperates with the ultrasound locating transducer 10 to produce an ultrasound B-image that is displayed on the monitor 20. Dependent on the output signal of the position sensor 17, the control and imaging unit 19 mixes a mark WZ' into the ultrasound image that identifies the center of the working zone.

In addition to containing the image-generating electronics required for generating ultrasound images, the control and imaging unit 19 contains all circuits that are required for driving the adjustment units 15 and 16 as well as for driving the ultrasound resonators 3.

For implementing a treatment, the coupling membrane 2 of the ultrasound applicator is applied to the perineum of the patient to be treated in a manner such that no air bubbles are enclosed between the body surface and the coupling membrane 2. Thereafter, the generation of ultrasound images is started by an appropriate actuation of the keyboard 21. Likewise on the basis of a corresponding actuation of the keyboard 21, the adjustment units 15 and 16 are now actuated such that an alignment of the ultrasound locating transducer 10 relative to the body of the patient is achieved wherein the prostate 9 is clearly portrayed in the ultrasound image. A region of the prostate 9 to be treated can now be marked with a light pen 20 or a similar input means. In response to a corresponding actuation of the keyboard 21, the control and imaging unit 19 now actuates the adjustment unit 15 such that the working zone WZ is displaced into that region of the prostate 9 that corresponds to the region marked with the light pen 22 in the ultrasound image. This is shown in the ultrasound image by the mark WZ' coming into coincidence with the region marked with the light pen 22 after the actuation of the adjustment unit 15. When such coincidence is achieved, the control and imaging unit 19 drives the ultrasound resonators 3 to generate ultrasound.

For the treatment of benign prostate hyperplasia, such a quantity of ultrasound energy is applied to the prostate tissue located in the working zone WZ such that the cell protein coagulates, leading to the necrotization of the prostate tissue. The necrotic tissue is dissimilated by metabolic processes.

There is, moreover, also the possibility of tracing the contours of the region of the prostate 9 to be therapeutically treated with the light pen 22. In response to an appropriate actuation of the keyboard 21, the working zone WZ is then displaced step-by-step within the region traced by the light pen 22 upon activation of the ultrasound resonators 3 such that the entire traced region is charged with ultrasound waves and necrotized.

The temperatures required for the necrotization of tissue usually lie beyond 45° C. For treating tumors in the urogenital region, however, it can be expedient to set the dose of ultrasound energy supplied to the tissue located in the working zone such that a temperature below 45° C., preferably approximately 43° C., results. This type of treatment, known as local hyperthermia, does not yet lead to the coagulation of the cell protein. On the contrary, the cell metabolism is disturbed, the consequence being a retardation in the growth of the tumor or even a regression of the tumor. It must be assured that no temperatures above 45° C. occur in the case of local hyperthermia, since this would unintentionally lead to necrotizations.

Focusing of the ultrasound waves on the basis of corresponding shaping of the ultrasound resonators can ensue instead of the focusing of the ultrasound waves emanating from the ultrasound resonators 3 with the positive lenses 4.

In the exemplary embodiment that has been set forth, the ultrasound waves are generated with two ultrasound resonators 3 arranged in a V-shaped orientation. Other solutions are possible within the scope of the invention. For example, a single ultrasound resonator can be employed, this being fashioned as a rectangular portion of a spherical cap-shaped piezoelectric transducer. It is also conceivable to employ an ultrasound resonator fashioned in the form of a linear array. In this case, electronic focusing would be employed in a known way. There is also the possibility of forming the ultrasound resonator as a plurality of individual resonators arranged mosaically. It is critical in all of these cases that an oblong cross section of the ultrasound waves be created, because it is such a cross section that allows an unimpeded propagation of the ultrasound waves to the prostate, given a perineal arrangement of the ultrasound applicator.

Although modifications and changes may be suggested by those skilled in the art, it is the intention of the inventor to embody within the patent warranted hereon all changes and modifications as reasonably and properly come within the scope of his contribution to the art.

I claim as My Invention:

1. A therapeutic ultrasound applicator for the urogenital region comprising:
a housing containing an acoustic propagation medium and having an exit surface adapted for non-invasive placement against a patient; and
ultrasound generator means, having a working axis, for generating focused ultrasound waves converging to a working region and which always have a cross section completely occupied by said ultrasound waves in a plane proceeding at a right angle relative to said working axis circumscribed by an envelope having a first principal axis intersecting said working axis and a second principal axis intersecting said first principal axis at substantially a right angle, said first principal axis having a length exceeding a length of said second principal axis, and said ultrasound waves exiting through said exit surface.

2. A therapeutic ultrasound applicator as claimed in claim 1 wherein said first principal axis has a length exceeding said second principal axis by at least a factor 1.5.

3. A therapeutic ultrasound applicator as claimed in claim 1 wherein said length of said first principal axis exceeds said length of said second principal axis at least by a factor 2.

4. A therapeutic ultrasound applicator as claimed in claim 1 wherein said ultrasound generator means comprises two substantially circular shaped focused ultrasound resonators disposed in V-shaped orientation, each ultrasound resonator having a focus and the foci of said ultrasound resonators being disposed in said working region.

5. A therapeutic ultrasound applicator as claimed in claim 1 wherein said exit surface comprises a resilient coupling membrane.

6. A therapeutic ultrasound applicator as claimed in claim 1 further comprising:
a support member disposed in said housing and having a support surface;
a carrier member, to which said ultrasound generator means is attached, disposed in said housing and having a carrier surface mating with said support surface, said support surface and said carrier surface having a cooperating shape for permitting spherical adjustment of the position of said working region.

7. A therapeutic ultrasound applicator as claimed in claim 6 further comprising means for mounting said support member in said housing for permitting axial displacement of said support member relative to said housing.

8. A therapeutic ultrasound applicator as claimed in claim 1 further comprising an ultrasound locating means for generating an image of said working region, said ultrasound locating means including an ultrasound locating transducer contained in an ultrasound applicator disposed in said ultrasound generator means.

9. A therapeutic ultrasound applicator as claimed in claim 8 wherein said ultrasound locating transducer is disposed on said working axis.

10. A therapeutic ultrasound applicator as claimed in claim 8 wherein said ultrasound locating transducer has a longitudinal axis, and further comprising means for mounting said ultrasound locating transducer for permitting displacement of said ultrasound locating transducer along said longitudinal axis.

11. A therapeutic ultrasound applicator as claimed in claim 8 wherein said ultrasound locating transducer has a longitudinal axis and further comprising means for mounting said ultrasound locating transducer for permitting rotation around said longitudinal axis.

12. A therapeutic ultrasound applicator for the human male urogenital region comprising:
a housing containing an acoustic propagation medium and having an exit surface adapted for placement against a human male subject; and
ultrasound generator means contained in said housing for emitting ultrasound waves through said exit surface propagating along a working axis and focused onto a working region, said ultrasound waves having a non-circular cross section completely occupied by said ultrasound waves in a plane perpendicular to said working axis and adapted to always cause said ultrasound waves to pass unimpeded between the pelvic bones of said subject when said housing is placed with said exit surface between the scrotum and rectum of said subject.

13. A therapeutic ultrasound applicator for the urogenital region comprising:
a housing containing an acoustic propagation medium and having an exit surface adapted for non-invasive placement against a patient; and
ultrasound generator means for generator focused acoustic waves converging to a working region, said ultrasound generator means having an emission surface from which said ultrasound waves emanate and a working axis along which said ultrasound waves propagate, said emission surface having a shape such that said ultrasound waves have a cross section in a plane proceeding at a right angle relative to said working axis completely occupied by said ultrasound waves and circumscribed by an envelope having a first principal axis intersecting said working axis and a second principal axis intersecting said first principal axis at substantially a right angle, said first principal axis having a length exceeding a length of said second principal axis, and said ultrasound waves exiting through said exit surface.

14. A method for human male prostate treatment comprising the steps of:
providing a housing containing an acoustic propagation medium and an ultrasound generator and having an exit surface;
placing said housing at an orientation relative to a human male subject having a prostate to be treated with said surface against said subject between the scrotum and rectum;
emitting ultrasound waves from said ultrasound generator in said housing, said ultrasound waves propagating along a working axis through said acoustic medium and said exit surface; and
focusing said ultrasound waves onto a working region so that said ultrasound waves have a non-circular cross section in a plane perpendicular to said working axis completely occupied by said ultrasound waves for causing said ultrasound waves to pass unimpeded between the pelvic bones of said subject when said housing is placed at said orientation relative to said subject.

* * * * *